United States Patent [19]
Tunley

[11] Patent Number: 5,919,674
[45] Date of Patent: Jul. 6, 1999

[54] COPPER RECOVERY

[75] Inventor: Trevor H. Tunley, Johannesburg, South Africa

[73] Assignee: Billiton SA Limited, South Africa

[21] Appl. No.: 09/048,430

[22] Filed: Mar. 26, 1998

[30]     Foreign Application Priority Data

Mar. 27, 1997  [ZA]  South Africa ............................ 97/2657

[51] Int. Cl.$^6$ ....................................................... C12P 3/00
[52] U.S. Cl. ............................................................ 435/168
[58] Field of Search ............................................. 435/168

[56]              References Cited

U.S. PATENT DOCUMENTS 4,256,485  3/1981  Richardson ............................. 435/168
4,497,778  2/1985  Pooley ..................................... 435/168

OTHER PUBLICATIONS

Biotech Abstract 84–00731 Short et al "Rx. for leaching copper: go the biological way" Chem Eng. 90, 14 26–27, 29, 1983.

*Primary Examiner*—Herbert J. Lilling
*Attorney, Agent, or Firm*—Locke Reynolds

[57]              ABSTRACT

A process for the recovery of copper from a copper sulphide concentrate in slurry form. The slurry is subjected to a biological oxidation turning the copper sulphide to soluble copper sulphate. The liquid containing the copper sulphate is separated from the slurry and treated with an oxime solvent extraction reagent so that copper ions are exchanged by the reagent for hydrogen ions to produce a raffinate which is high in sulphuric acid and low in copper sulphate. The solvent extraction reagent is then stripped from the raffinate with a sulphuric acid solution. Copper is electrically harvested from the sulphuric acid solution and the copper depleted raffinate can be returned to again form a slurry with additional ore for subsequent biological oxidation. The preferred bacterium is one of Thiobacillus Ferro-oxidans, Thiobacillus Thio-oxidans, Leptospirrilum Ferro-oxidans, Thiobacillum Caldus, and Sulpholobus.

12 Claims, 2 Drawing Sheets

COPPER RECOVERY

BACKGROUND OF THE INVENTION

This invention relates to the recovery of copper. Copper recovery from copper sulphide concentrates is usually accomplished by pyrometallurgical processes. Copper concentrates which may be recovered by froth flotation are dried and smelted in many types of furnaces to a copper matte which is further refined to copper metal.

Hydrometallurgical treatment methods have been developed and many processes have been reported. Very few have, to the applicant's knowledge, been taken to commercial reality.

Copper is often recovered by solvent extraction and electrowinning, but this process is normally applied to oxide ores. Sulphide copper ores of low grade are treated by dump leaching and heap leaching. The solutions generated in this way are treated by solvent extraction and electrowinning to produce pure copper metal at the cathode. Bacterial action may also be responsible for the dissolution of copper.

Copper concentrates with acid soluble copper are sometimes treated by leaching in agitated tanks with a suitable acid such as sulphuric acid. The solutions can either be processed directly by electrowinning or can be processed through solvent extraction before electrowinning.

Many copper concentrates are low in grade and this makes smelting expensive. Some copper concentrates contain elements such as arsenic which make their processing by smelting objectionable. Smelting companies are reluctant to purchase concentrates, and apply penalties according to the content and nature of such elements.

Dissolution of copper concentrates is known. Copper minerals such as chalcocite, bornite, covellite, digenite, enargite and tetrahedrite will dissolve in ferric sulphate. Other leaching agents such as ferric chloride and ammonia are used, but there are drawbacks relating to their corrosive nature or their cost.

Ferric sulphate is a leaching reagent which can be used for the copper minerals mentioned, but its disadvantage is that the reagent is consumed and converts to ferrous sulphate. The solution must either be very concentrated in ferric sulphate or the amount of copper concentrate treated must be very small in relation to the solution volume. This means a large ratio of solution to solids.

Bacterial action is known to be able to convert ferrous sulphate to ferric sulphate. Advantage can be taken of this phenomenon to regenerate ferric sulphate during leaching. Thus a smaller volume of solution can be used, because the ferric sulphate leaching agent is repeatedly used to leach more concentrate. As an example, the leaching of the mineral chalcocite takes place in the following manner:

$$CU_2S+2FE_2(SO_4)_3 \rightarrow 2CuSO_4+4FeSO_4+S$$

Ferrous sulphate can be regenerated by bacterial action. Air is blown into an agitated tank where leaching and regeneration take place simultaneously in accordance with the following equation:

$$4FeSO_4+2H_2SO_4+O_2 \rightarrow 2Fe_2(SO_4)_3+2H_2O$$

There is a disadvantage in this procedure for sulphuric acid must be added to the agitated tank to satisfy the second reaction. Some sulphuric acid is generated by bacterial action whereby sulphur which is formed in the first reaction is oxidised to sulphuric acid, but it is insufficient to satisfy the oxidation reaction:

$$S+{}^3/_2O_2+H_2) \rightarrow H_2SO_4$$

If the three reactions are added together it is found that sulphuric acid must still be added to the agitated reactor:

$$Cu_2S+H_2SO_4+{}^5/_2O_2 \rightarrow 2CuSO_4+H_2O$$

SUMMARY OF THE INVENTION

The invention provides a process for the recovery of copper which includes the following steps:

(a) biologically oxidising copper sulphide concentrate in slurry form to dissolve copper as soluble copper sulphate;

(b) subjecting the slurry to solid/liquid separation to produce a solution with a high copper concentration;

(c) treating the solution with a solvent extraction reagent so that copper ions are exchanged by the reagent for hydrogen ions to produce a raffinate which is high in sulphuric acid and low in copper sulphate;

(d) stripping the solvent extraction reagent with a sulphuric acid solution;

(e) electrowinning copper from the sulphuric acid solution; and (f) using at least a portion of the raffinate from step (c) in step (a).

In step (a) iron in solution is constantly reoxidised to ferric sulphate making use of air, together with sulphuric acid which is introduced in the solution used to form a slurry. As indicated, at least part of the sulphuric acid requirement is derived from the raffinate.

The ratio of concentrate to solution prior to the solvent extraction step (c), i.e. in the feed to the solvent extraction step, may be adjusted e.g. by altering the ratio of raffinate to concentrate, to give a copper concentration in solution in excess of 10 grams per liter, preferably in excess of 20 grams per liter and desirably of from 25 to 30 grams per liter.

To achieve this desired high level of copper concentration the leachate must be concentrated beforehand to a higher level, for the leachate is filtered and washed and this dilutes the concentrate.

The biological oxidation in step (a) may be carried out using any suitable bacterium or bacteria. Depending on the mineral type, use may for example be made of one or more mesophiles or thermophiles such as the following: Thiobacillus Ferro-oxidans, Thiobacillus Thio-oxidans, Leptospirrilum Ferro-oxidans, Thiobacillum Caldus and Sulpholobus.

A combination of mesophiles such as Thiobacillus Ferro-oxidans, Thiobacillus Thio-oxidans and Leptospirrilum Ferro-oxidans may be used for the oxidation of chalcocite, bornite, covellite, digenite, enargite and tetrahedrite. If these bacteria are used then the temperature in the tank used for carrying out step (a) may be maintained at a value of up to about 45° C.

Moderate thermophiles such as Thiobacillus Caldus and extreme thermophiles such as Sulpholobus may be used for the leaching of chalcopyrite. The temperature of the tank used for carrying out step (a) may then be maintained at a value of from about 50° C. to 80° C., depending on the optimum temperature environment for the bacteria.

Step (b) may be carried out in any suitable way and, for example, use may be made of settling or filtration.

Wash water may be introduced in step (b) to ensure that the solid residue is washed free of copper sulphate.

Step (c) may be carried out using any appropriate solvent extraction reagent such as an oxime-type reagent.

Preferably steps (b) and (c) are controlled so that the raffinate contains from 30 to 40 grams per liter free sulphuric acid. The copper content may lie in the range of from 2 to 5 grams per liter. This copper content is not necessarily disadvantageous for as much as possible of the raffinate is recycled.

The concentration level of sulphuric acid in the raffinate is dependent at least on the nature of the solvent extraction reagent which is used in step (c). This level should, within reason, be as high as possible. However solvent extraction reagents which are currently available and which are known to the applicant do not readily permit a concentration of sulphuric acid materially in excess of 40 grams per liter to be attained.

According to a variation of the invention the excess raffinate, ie. the raffinate which is not used in step (a), is treated in any appropriate way. One version of the invention makes use of the fact that the copper concentrate itself often contains carbonate minerals which consume sulphuric acid. Thus, as an option, the excess raffinate is contacted with the copper concentrate prior to step (a). This consumes sulphuric acid and dissolves some acid soluble copper to produce a solution which, after solid/liquid separation, is subjected to solvent extraction.

Another variation of the invention relies on the fact that there is often a reserve of oxide copper or acid soluble copper at any site where copper sulphides are situated. The excess raffinate is used to leach oxide copper to produce a more concentrated copper solution which is also suitable for solvent extraction and subsequent treatment either in conjunction with step (d) and (e) or separately therefrom. This leaching may be carried out either by heap leaching or in an agitated tank leaching system.

BRIEF DESCRIPTION OF THE DRAWINGS

The invention is further described by way of examples with reference to the accompanying drawings in which.

DESCRIPTION OF PREFERRED EMBODIMENTS

Figure 1:
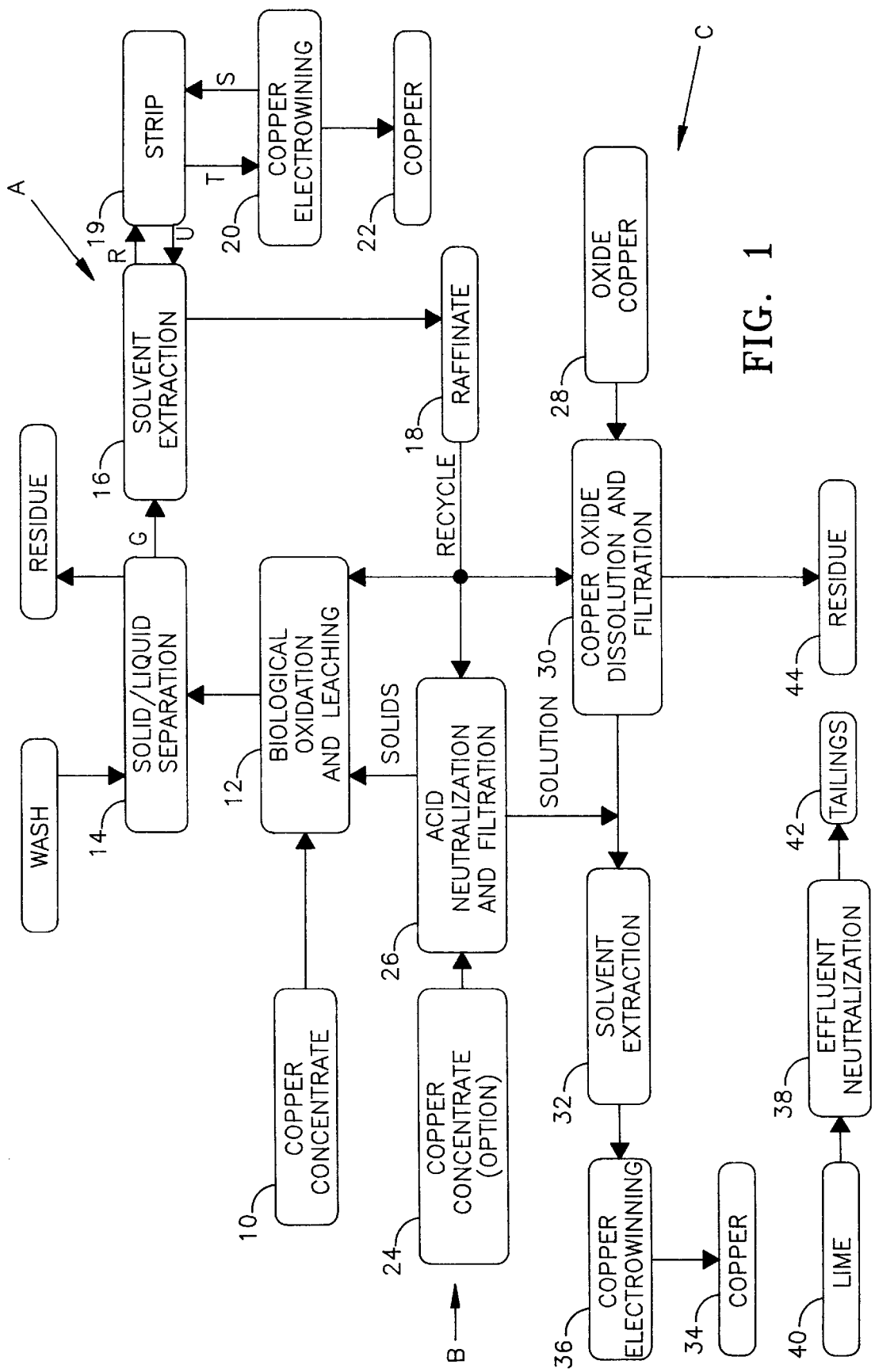
FIG. 1 illustrates in block diagram form the basic process of the invention, and two optional additional techniques for the treatment of excess raffinate.

FIG. 1 of the accompanying drawings illustrates in block diagram three sections marked A, B and C respectively.

Section A illustrates a basic process for the recovery of copper from a copper sulphate concentrate according to the invention while sections B and C respectively illustrate optional additional processes for the treatment of raffinate produced in the method of the invention.

Referring to Section A copper concentrate 10 is treated in a bacterial oxidation system 12 which consists of several agitated tanks in series, with air addition.

The bacterium or bacteria used for the biological oxidation depend on the nature of the sulphide concentrate. For example one or more of the following, and preferably all three, are used for the bacterial leaching of chalcocite, bornite, covellite, digenate, enargite and tetrahedrite: Thiobacillus Ferro-oxidans, Thiobacillus Thio-oxidans and Leptospirrilum Ferro-oxidans. These bacteria are effective at temperatures up to about 45° C. and the temperature of the tank or tanks in which the oxidation is carried out is maintained at an optimum value. On the other hand a sulphide concentrate such as chalcopyrite is not easily oxidised by these bacteria. Moderate or extreme thermophilic bacteria are however effective on chalcopyrite. These bacteria are not well characterised and several strains have been reported. Extreme thermophiles are generally described under the name Sulpholobus and a number of strains which are effective at temperatures of about from 70° C. to 80° C. are reported in the literature. Moderate thermophiles such as Thiobacillus Caldus are effective at lower temperatures, of from about 50° C. to 60° C.

If extreme thermophiles are used then the temperature of the agitated tank or tanks is maintained at an optimum value which depends on the particular strain of Sulpholobus actually used, with a typical value being in the range of from 70° C. to 80° C.

Copper is dissolved from the copper sulphide concentrates as soluble copper sulphate. Iron in solution is constantly reoxidised to ferric sulphate using air and sulphuric acid which is introduced as the solution used to form a slurry. The ratio of concentrate to solution is adjusted to give a copper concentration in the feed to the solvent extraction step (c) of from 20 to 25 grams per liter.

The slurry leaving the biological system 12 consists of a solution of copper sulphate and ferric sulphate and is subjected to a solid/liquid separation step 14. Residue solids can be separated from the solution in any appropriate way and for example use may be made of counter-current decantation or by filtration or both. Wash water is introduced to ensure that the solid residue is free of copper sulphate and in this way the solution, which prior to washing should have a copper concentration of from 30 to 40 grams per liter, is diluted to 20 to 25 grams of copper per liter.

The clean solution, which is free of solids, is subjected to a solvent extraction step 16 wherein a solvent extraction reagent exchanges copper ions for hydrogen ions so that the solution (the raffinate) is high in sulphuric acid and low in copper sulphate. The sulphuric acid concentration should be as high as possible but this depends on the nature of the solvent extraction reagent used. Currently available reagents produce sulphuric acid concentrations of up to 30 to 40 grams per liter. Use may be made of oxime-type reagents which are commercially available for the solvent extraction of the copper. The copper is removed, being displaced by sulphuric acid.

It is important to have the copper concentration in the feed to the solvent extraction unit at as high a level as possible. The raffinate 18 leaving the step 16 will then contain from 30 to 40 grams per liter of sulphuric acid.

As much as possible of the raffinate 18 is used to feed the biological leach system for the sulphuric acid contained therein can be used to satisfy the sulphuric acid requirements of the biological leach system. Thus a large proportion of the raffinate is used to repulp the concentrate which is fed to the system 12.

The solvent extraction reagent R which is loaded with copper is stripped in a phase 19 with a strong sulphuric acid solution S which is the spent electrolyte from an electrowinning step 20. A strong electrolyte T passes from the phase 19 to the electrowinning step 20 wherein copper is electrowon, and stripped solvent U is returned from the phase 19 to the solvent extraction step 16.

The raffinate which is not used in the biological oxidation step 12 can be treated or used in different ways illustrated, for example, in sections B and C of FIG. 1.

The copper concentrate itself often contains carbonate materials which consume sulphuric acid. Thus, as an option (section B), the excess raffinate can be contacted with the copper concentrate 24 in a step 26 before the biological oxidation step. This consumes sulphuric acid and dissolves some acid soluble copper. The solution after solid/liquid separation is subjected to solvent extraction. The final raffinate can be used as make up water or for washing the residue.

Section C illustrates another optional feature which relates to the treatment of the excess raffinate used by sulphate extraction.

Conventional solvent extraction of copper produces solutions which are low in copper. The solutions may be recycled to heap leaching or are discarded after neutralization and are disposed of on tailings dams.

The method of section A produces a solution which, after treatment by solvent extraction, is concentrated and the raffinate can contain from 2 to 5 grams copper per liter with from 30 to 40 grams per liter of free sulphuric acid. This copper concentration is similar to the feed concentration of conventional solvent extraction systems.

There is frequently a reserve of copper oxide or acid soluble copper at any site where copper sulphides are situated. The oxide copper, designated 28, can be leached by the excess raffinate either by heap leaching or in an agitated tank leaching system 30. Further copper will enter the solution which will then be suitable for solvent extraction in a step 32. Copper 34 can be electrowon from the solution by means of a process 36.

The solvent extraction and electrowinning processes can be separate from the similar phases of section A, or use can be made of the same systems 16 and 20 respectively, if required.

The effluent produced by the solvent extraction step 32 is neutralized in a phase 38 by the addition of lime 40 and the tailings 42 are disposed of on suitable dams. Similarly the residue 44 from the leaching step 30 is disposed of on a tailings dam.

Copper concentrates often contain some cobalt which will also be solubilised by the biological oxidation. As a large portion of the raffinate 18 is recycled to the phase 12 the concentration of cobalt increases.

It is possible to recover the cobalt from the excess raffinate after solvent extraction for copper. This is done by solvent extraction reagents which are specific for cobalt or by selective precipitation. These methods require careful neutralization to a controlled pH before solvent extraction or precipitation of cobalt.

Available solvent extraction reagents enable the selective extraction of copper over iron to be achieved. These reagents are however more selective with regard to iron in ferrous form than in ferric form. The ferric form thus accumulates and must be bled from the system when it reaches unacceptable concentration levels. This can be wasteful particularly in a system in which cobalt is used to enhance the extraction process for the cobalt is continuously bled from the system.

Figure 2:
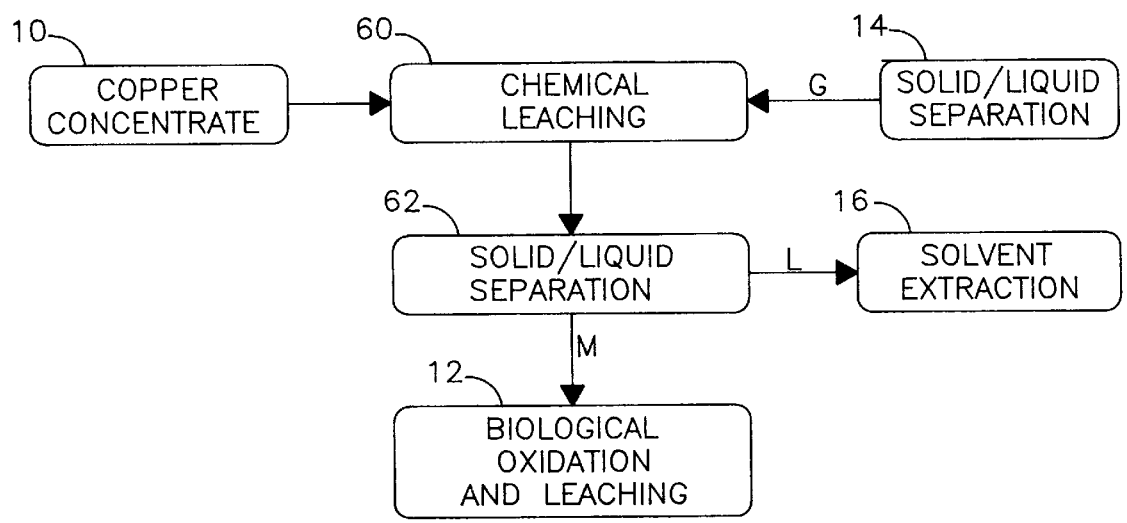
FIG. 2 illustrates a variation of the basic process of FIG. 1.

FIG. 2 illustrates a variation of the basic process shown in FIG. 1 which is directed to addressing this problem.

The feed G from the separation stage 14 to the solvent extraction step 16 is diverted and used to chemically pre-leach the copper concentrate 10, in a step 60. The leachate is subjected to a solid/liquid separation step 62 and the liquid L is then diverted to the solvent extraction step 16, for treatment and processing in the manner which has been described hereinbefore. The solids M are then subjected to the biological oxidation and leaching step 12, in the manner which has been described hereinbefore.

This pre-leaching treatment holds important benefits. The iron which prior to the step 60 existed in the ferric form is converted to the ferrous form and, as stated, this is highly desirable for the efficient selective extraction of copper in the step 16. Another benefit is that the pre-leaching, which is done relatively quickly, reduces the duration of the step 12. This in turn reduces the likelihood that pyrite will be dissolved during step 12.

I claim:

1. A process for the recovery of copper which includes the following steps:

(a) biologically oxidising copper sulphide concentrate in slurry form to dissolve copper as soluble copper sulphate;

(b) subjecting the slurry to solid/liquid separation to produce a solution with a high copper concentration;

(c) treating the solution with a solvent extraction reagent so that copper ions are exchanged by the reagent for hydrogen ions to produce a raffinate which is high in sulphuric acid and low in copper sulphate;

(d) stripping the solvent extraction reagent with a sulphuric acid solution;

(e) electrowinning copper from the sulphuric acid solution; and (f) using at least a portion of the raffinate from step (c) in step (a).

2. A process according to claim 1 wherein the copper concentration of the solution produced in step (b) is greater than 10 grams per liter.

3. A process according to claim 2 wherein the said copper concentration is greater than 20 grams per liter.

4. A process according to claim 3 wherein the said copper concentration is in the range of from 25 to 30 grams per liter.

5. A process according to claim 1 wherein the biological oxidation in step (a) is carried out using one or more of the following bacteria: Thiobacillus Ferro-oxidans, Thiobacillus Thio-oxidans, Leptospirrilum Ferro-oxidans at a temperature of up to about 45° C.

6. A process according to claim 1 wherein the biological oxidation in step (a) is carried out using thermophilic bacteria at a temperature in the range of from 50° C. to 80° C.

7. A process according to claim 1 wherein step (b) is carried out using settling or filtration.

8. A process according to claim 1 wherein, in step (c), use is made of an oxime reagent.

9. A process according to claim 1 wherein steps (b) and (c) are controlled so that the raffinate in step (c) contains from 30 to 40 grams per liter free sulphuric acid.

10. A process according to claim 1 wherein any raffinate, remaining as a result of step (f) and not used in step (a), is contacted with the copper sulphide concentrate prior to step (a).

11. A process according to claim 1 wherein any raffinate, remaining as a result of step (f) and not used in step (a), is used in steps (d) and (e) to leach oxide copper to produce a solution from which copper is obtained by solvent extraction and electrowinning.

12. A process according to claim 1 further comprising the steps of:

(i) using a portion of the high copper concentration solution produced in step (b) to chemically pre-leach the copper sulphide concentrate prior to introduction of the copper sulphide concentrate into step (a), (ii) subjecting the leachate from step (i) to a solid/liquid separation step, (iii) directing the separated liquid from step (ii) to the solvent extraction step (c), and (iv) subjecting the separated solids of step (ii) to the biological oxidation step (a).

* * * * *